United States Patent
Sava Gallis et al.

(10) Patent No.: US 12,391,977 B2
(45) Date of Patent: Aug. 19, 2025

(54) MIXED CLUSTER HETEROMETALLIC METAL-ORGANIC FRAMEWORKS FOR COMPLEX OPTICAL TAGS

(71) Applicant: National Technology & Engineering Solutions of Sandia, LLC, Albuquerque, NM (US)

(72) Inventors: Dorina F. Sava Gallis, Albuquerque, NM (US); Kimberly S. Butler, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 314 days.

(21) Appl. No.: 18/080,051

(22) Filed: Dec. 13, 2022

(65) Prior Publication Data
US 2023/0115755 A1    Apr. 13, 2023

Related U.S. Application Data

(63) Continuation-in-part of application No. 17/479,710, filed on Sep. 20, 2021, now Pat. No. 11,767,468.
(Continued)

(51) Int. Cl.
C12Q 1/68    (2018.01)
C09B 57/00   (2006.01)
(Continued)

(52) U.S. Cl.
CPC ............ *C12Q 1/6816* (2013.01); *C09B 57/00* (2013.01); *C09K 11/06* (2013.01);
(Continued)

(58) Field of Classification Search
CPC ........ C12Q 1/6816; C09B 57/00; C09K 11/06
See application file for complete search history.

(56) References Cited

U.S. PATENT DOCUMENTS 8,742,152 B2 *  6/2014  Yaghi ............... C07F 7/003
                                              556/113
8,916,722 B2 * 12/2014  Yaghi ............... B01J 20/226
                                              556/132
(Continued)

OTHER PUBLICATIONS

Griffin et al., Uncovering the Structural Diversity of Y(III) Naphthalene-2,6-Dicarboxylate MOFs through Coordination Modulation, Frontiers in Chemistry 7:36, published: Jan. 31, 2019, doi: 10.3389/fchem.2019.00036, www.frontiers in.org) (Year: 2019).*

(Continued)

*Primary Examiner* — Hugh Maupin
(74) *Attorney, Agent, or Firm* — Kevin W. Bieg

(57) ABSTRACT

A rapid and facile design strategy to create a highly complex optical tag with programmable, multimodal photoluminescent properties is described. This is achieved via intrinsic and biomolecule-fluorophore hidden signatures. As a first covert feature of the tag, an intricate novel heterometallic near-infrared (NIR) emitting mesoporous metal-organic framework (MOF) was synthesized comprising homometallic hexanuclear clusters based on Nd and Yb. To generate controlled, multimodal, and tailorable emission with difficult to counterfeit features, the NIR emissive MOF was post-synthetically modified via a fluorescent biomolecule labeling design strategy. The surface attachment of several distinct fluorophores, including the simultaneous attachment of up to three distinct fluorescently labeled DNA oligos was demonstrated, with excitation and emission properties across the visible spectrum (480-800 nm). The DNA inclusion as a secondary covert element in the tag was demonstrated via detection of SYBR Gold dye association.

22 Claims, 11 Drawing Sheets

Related U.S. Application Data

(60) Provisional application No. 63/086,419, filed on Oct. 1, 2020.

(51) Int. Cl.
   | | |
   |---|---|
   | *C09K 11/06* | (2006.01) |
   | *C12Q 1/6816* | (2018.01) |
   | *G01N 21/64* | (2006.01) |
   | *G01N 33/58* | (2006.01) |

(52) U.S. Cl.
   CPC ....... *G01N 21/6428* (2013.01); *G01N 33/582* (2013.01); *C09K 2211/182* (2013.01); *G01N 2021/6439* (2013.01)

(56) References Cited

U.S. PATENT DOCUMENTS

| | | | |
|---|---|---|---|
| 2007/0141727 A1* | 6/2007 | Huang | A61K 49/0065 436/526 |
| 2012/0039810 A1* | 2/2012 | Gorenstein | A61P 35/00 424/9.1 |
| 2016/0047816 A1* | 2/2016 | Stern | B82Y 15/00 435/6.19 |
| 2021/0146378 A1* | 5/2021 | Hinestrosa Salazar | B03C 5/005 |

OTHER PUBLICATIONS

Sava Gallis, D. et al., "Programmable Photoluminescence via Intrinsic and DNA-Fluorophore Association in a Mixed Cluster Heterometallic MOF," ACS Applied Materials Interfaces, 2022, vol. 14, pp. 10566-10576.

White, K. A. et al., "Near-Infrared Luminescent Lanthanide MOF Barcodes," Journal of the American Chemical Society, 2009, vol. 131, pp. 18069-18071.

Wang, J. et al., "Multi-Emissive Lanthanide-Based Coordination Polymers for Potential Application as Luminescent Bar-Codes," Inorganic Chemistry, 2019, vol. 58, pp. 2659-2668.

Zhang, H-B et al., "Digital Controlled Luminescent Emission via Patterned Deposition of Lanthanide Coordination Compounds," ACS Applied Materials Interfaces, 2014, vol. 6, pp. 12594-12599.

Deneff, J. I. et al. "Encoding Multilayer Complexity in Anti-Counterfeiting Heterometallic MOF-Based Optical Tags," Angewandte Chemie International Edition, 2021, vol. 60, pp. 1203-1211.

Gao, Z. et al., "Spatially Responsive Multicolor Lanthanide-MOF Heterostructures for Covert Photonic Barcodes," Angewandte Chemie International Edition, 2020, vol. 59, pp. 19060-19064.

Abednatanzi, S. et al., "Mixed-Metal Metal-Organic Frameworks," Chem. Soc. Rev., 2019, vol. 48, pp. 2535-2565.

Massomi, M. et al., "Mixed Metal MOFs: Unique Opportunities in Metal-Organic Framework (MOF) Functionality and Design," Angewandte Chemie International Edition, 2019, vol. 58, pp. 15188-15205.

Xue, D-H. et al., "Tunable Rare-Earth fcu-MOFs: A Platform for Systematic Enhancement of $CO_2$ Adsorption Energetics and Uptake," Journal of the American Chemical Society, 2013, vol. 135, pp. 7660-7667.

Sava Gallis, D. et al., "Multifunctional, Tunable Metal-Organic Framework Materials Platform for Bioimaging Applications," ACS Applied Materials Interfaces, 2017, vol. 9, pp. 22268-22277.

Luebke, R. et al., "Versatile Rare Earth Hexanuclear Clusters for the Design and Synthesis of Highly-Connected ftw-MOFs," Chemical Science, 2015, vol. 6, pp. 4095-4102.

Sava Gallis, D. et al., "NOx Adsorption and Optical Detection in Rare Earth Metal-Organic Frameworks," ACS Applied Materials Interfaces, 2019, vol. 11, pp. 43270-43277.

Butler, K. S. et al., "Antibody Targeted Metal-Organic Frameworks for Bioimaging Applications," ACS Applied Materials Interfaces, 2020, vol. 12, pp. 31217-31224.

Henkelis, S. E. et al., "Kinetically Controlled Linker Binding in Rare Earth-2,5-Dihydroxyterepthalic Acid Metal-Organic Frameworks and Its Predicted E ects on Acid Gas Adsorption," ACS Applied Materials Interfaces, 2021, vol. 13, pp. 56337-56347.

Guillerm, V. et al., "Discovery and introduction of a (3,18)-connected net as an ideal blueprint for the design of metal-organic frameworks," Nature Chemistry, 2014, vol. 6, pp. 673-680.

Abdulhalim, R. G. et al., "A Fine-Tuned Metal-Organic Framework for Autonomous Indoor Moisture Control," Journal of the American Chemical Societyy, 2017, vol. 139, pp. 10715-10722.

Quezanda-Novoa, V. et al., "Building a shp: A Rare-Earth Metal-Organic Framework and Its Application in a Catalytic Photooxidation Reaction," Chemistry of Materials, 2021, vol. 33, pp. 4163-4169.

Alezi, D. et al., "Quest for Highly Connected Metal-Organic Framework Platforms: Rare-Earth Polynuclear Clusters Versatility Meets Net Topology Needs," Journal of the American Chemical Society, 2015, vol. 137, pp. 5421-5430.

Cheisson, T. and Schelter, E. J., "Rare Earth Elements: Mendeleev's Bane, Modern Marvels," Science, 2019, vol. 363, pp. 489-493.

Zucchi, G. et al., "Structural Diversity in Neodymium Bipyrimidine Compounds with Near Infrared Luminescence: from Mono- and Binuclear Complexes to Metal-Organic Frameworks," Inorganic Chemistry, 2008, vol. 47, pp. 10398-10406.

Su, K. et al., "Syntheses, Structures, Luminescence and Magnetic Properties of Three High-Nuclearity Neodymium Compounds Based on Mixed Sulfonylcalix[4]arene-phosphonate Ligands," CrystEngComm, 2016, vol. 18, pp. 4921-4928.

Sava Gallis, D. et al., "Biocompatible MOFs with High Absolute Quantum Yield for Bioimaging in the Second Near Infrared Window," CrystEngComm, 2018, vol. 20, pp. 5919-5924.

Wang, Y. et al., "Metal-Organic Frameworks for Virus Detection," Biosensors and Bioelectronics, 2020, vol. 169, 112604.

Wu, F. et al., "Recent Advances in Fluorescence Sensors Based on DNA-MOF Hybrids," Luminescence, 2020, vol. 35, pp. 440-446.

Zhuang, J. et al., "Integration of Biomolecules with Metal-Organic Frameworks," Small, 2017, vol. 13, 1700880.

Morris, W. et al., "Nucleic Acid-Metal Organic Framework (MOF) Nanoparticle Conjugates," Journal of the American Chemical Society, 2014, vol. 136, pp. 7261-7264.

Kahn, J.S. et al., "Stimuli-Responsive DNA-Functionalized Metal-Organic Frameworks (MOFs)," Advanced Materials, 2017, vol. 29, 1602782.

Ning, W. et al., "Imparting Designer Biorecognition Functionality to Metal-Organic Frameworks by a DNA-Mediated Surface Engineering Strategy," Small, 2018, vol. 14, 1703812.

Wang, Z. et al., "Organelle-Specific Triggered Release of Immunostimulatory Oligonucleotides from Intrinsically Coordinated DNA-Metal-Organic Frameworks with Soluble Exoskeleton," Journal of the American Chemical Society, 2017, vol. 139, pp. 15784-15791.

Wang, S. et al., "General and Direct Method for Preparing Oligonucleotide-Functionalized Metal-Organic Framework Nanoparticles," Journal of the American Chemical Society, 2017, vol. 139, pp. 9827-9830.

Wang, S. et al., "DNA-Functionalized Metal-Organic Framework Nanoparticles for Intracellular Delivery of Proteins," Journal of the American Chemical Society, 2019, vol. 141, pp. 2215-2219.

Micklitz, W. and Lippard, S. J., "A Novel Hexairon (III) Aggregate Prepared for a Basic Iron (III) Benzoate. Possible Building Blocks in Ferritin Core Foundation." Inorganic Chemistry, 1988, vol. 27, pp. 3067-3069.

Ehsan, M. A. et al., "Deposition of Iron Titanate/Titania Ceramic Composite Thin Films from a Single Molecular," precursor, Inorganica Chimica Acta, 2011, vol. 376, pp. 189-194.

Baca, S. G. et al., "Avoiding Magnetochemical Overparametrization, Exemplified by One-Dimensional Chains of Hexanuclear Iron(III) Pivalate Clusters," Inorganic Chemistry, 2013, vol. 52, pp. 4154-4156.

(56) References Cited

OTHER PUBLICATIONS

Morris, W. et al., "Synthesis, Structure, and Metalation of Two New Highly Porous Zirconium Metal-Organic Frameworks," Inorganic Chemistry, 2012, vol. 51, pp. 6443-6445.

* cited by examiner

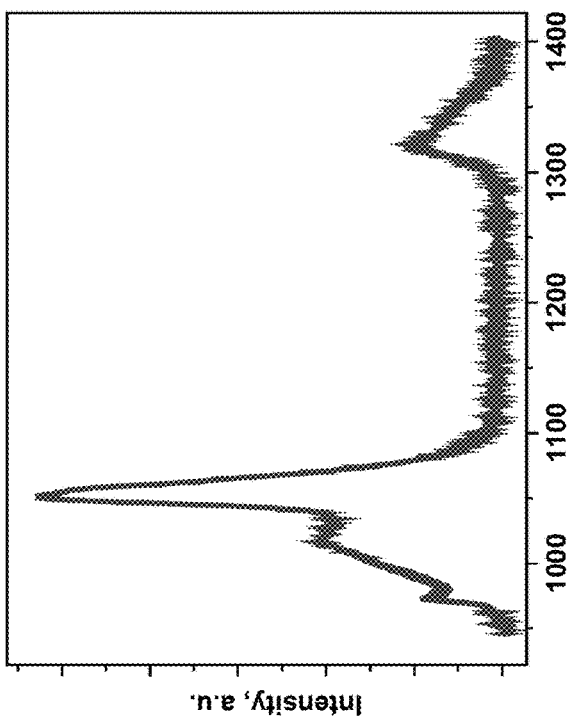
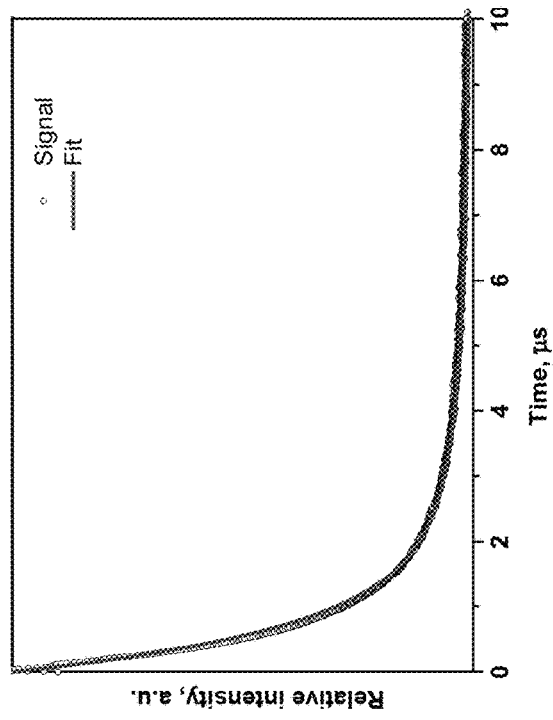
FIG. 5A
FIG. 5B

MIXED CLUSTER HETEROMETALLIC METAL-ORGANIC FRAMEWORKS FOR COMPLEX OPTICAL TAGS

CROSS-REFERENCE TO RELATED APPLICATIONS

This application is a continuation-in-part of U.S. application Ser. No. 17/479,710, filed Sep. 20, 2021, which claims the benefit of U.S. Provisional Application No. 63/086,419, filed Oct. 1, 2020, both of which are incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

STATEMENT REGARDING PRIOR DISCLOSURES BY THE INVENTOR OR A JOINT INVENTOR

The following disclosure is submitted under 35 U.S.C. 102(b)(1)(A): Dorina F. Sava Gallis, Kimberly S. Butler, Charles J. Pearce, Nichole Valdez, and Mark Q. Rodriguez, "Programmable Photoluminescence via Intrinsic and DNA-Fluorophore Association in a Mixed Cluster Heterometallic MOF," *ACS Applied Materials & Interfaces* 14(8), 10566 (2022). The subject matter of this disclosure was conceived of or invented by the inventors named in this application.

FIELD OF THE INVENTION

The present invention relates to optical tags and, in particular, to an optical tag comprising a mixed cluster heterometallic metal-organic framework.

BACKGROUND OF THE INVENTION

Optical tags afford methods to identify, track, and provide provenance for materials. An ideal tag is inexpensive to produce and detect, maintains high coding capacity, and has a complex signature to prevent duplication. Although common overt tags are coupled with easy detection, most current materials options are subject to counterfeiting. To circumvent this limitation, multiple types of nanomaterials are under development. See O. Guillou et al., *Acc. Chem. Res.* 49, 844 (2016); A. Abdollahi et al., *ACS Nano* 14, 14417 (2020); S. Shikha et al., *Chem. Soc. Rev.* 46, 7054 (2017); K. Bernot et al., *Acc. Chem. Res.* 54, 427 (2021); R. Maouche et al., *Inorg. Chem.* 60, 3707 (2021); and Q. Tang et al., *Inorg. Chem.* 53, 289 (2014). Although these materials can address the counterfeiting issue, many of these systems lack structural and compositional versatility which limits their extended applicability in this field. Also, the synthetic approaches for these materials are normally very elaborate.

Metal-organic frameworks (MOFs) concurrently possess several attributes to allow complex signatures for optical tags: (i) tunable optical properties for concomitant emission in the ultraviolet (UV), visible, and/or near infrared (NIR), making it an ideal intricate system to prevent counterfeiting; (ii) controllable multi-metal compositions allowing orthogonal confirmation of identity; and (iii) porosity and chemical tunability, to allow the design of environmentally responsive smart tags. See K. A. White et al., *J. Am. Chem. Soc.* 131, 18069 (2009); J. Wang et al., *Inorg. Chem.* 58, 2659 (2019); H.-B. Zhang et al., *ACS Appl. Mater. Interfaces* 6, 12594 (2014); J. I. Deneff et al., *Angew. Chem. Int. Ed.* 60, 1203 (2021); and Z. Gao et al., *Angew. Chem. Int. Ed.* 59, 19060 (2020).

The synthesis of MOFs built from more than one metal ion or type of cluster is uniquely attractive, as facilitated by the synergistic properties that are attained this way, including tandem catalysis, tunable electronic, and complex photophysical properties, to only name a few. See S. Abednatanzi et al., *Chem. Soc. Rev.* 48, 2535 (2019). Heterometallic MOFs have been scarcely explored in the context of the impressive body of MOF literature, in part due to the difficulty in controlling the coordination chemistry at the molecular level of the distinct metals. See M. Y. Masoomi et al., *Angew. Chem. Int. Ed.* 58, 15188 (2019).

Accessing the desired molecular building blocks with precision under pre-determined reaction coordinates greatly improves the design prospects in MOFs. Recently, great progress has been made in this direction with the discovery of rare earth (RE) element polynuclear clusters-based MOFs. A hexanuclear and a nonanuclear cluster emerged as the "default" molecular building blocks among MOFs constructed from RE polynuclear clusters. See D.-X. Xue et al., *J. Am. Chem. Soc.* 135, 7660 (2013); D. F. Sava Gallis et al., *ACS Appl. Mater. Interfaces* 9, 22268 (2017); R. Luebke et al., *Chem. Sci.* 6, 4095 (2015); D. F. Sava Gallis et al., *ACS Appl. Mater. Interfaces* 11, 43270 (2019); K. S. Butler et al., *ACS Appl. Mater. Interfaces* 12, 31217 (2020); S. E. Henkelis et al., *ACS Appl. Mater. Interfaces* 13, 56337 (2021); J. I. Deneff et al., *Angew. Chem. Int. Ed.* 60, 1203 (2021); V. Guillerm et al., *Nat. Chem.* 6, 673 (2014); R. G. AbdulHalim et al., *J. Am. Chem. Soc.* 139, 10715 (2017); and V. Quezada-Novoa et al., *Chem. Mater.* 33, 4163 (2021). Pioneering work from the Eddaoudi group recently described the access to both of these clusters in a concurrent fashion, highlighting the unique potential of polynuclear REs to meet yet to be realized topological needs and result in increased functionality in complex MOFs. See D. Alezi et al., *J. Am. Chem. Soc.* 137, 5421 (2015).

In this context, polynuclear RE-based MOFs represent ideal platforms to probe and overcome fundamental challenges in heterometallic MOF synthesis, as facilitated by the control over the molecular building blocks. Furthermore, while REs display chemical similarities as a distinctive group among other elements, at an individual level they possess subtle differences in their coordination characteristics and resulting properties. See T. Cheisson and E. J. Schelter, *Science* 363, 489 (2019). The difference in the ionic radii across the series, generally referred to as the "lanthanide contraction" is an important parameter to exploit in order to scope additional "on demand" design tools available to expand the MOF reticular chemistry repertoire.

SUMMARY OF THE INVENTION

The present invention is directed to an optical tag comprising a mixed cluster heterometallic metal-organic framework comprising a first rare earth-based cluster and at least one other rare earth-based cluster connected by carboxylic-acid based linkers. The invention is further directed to a method to synthesize the optical tag.

The invention provides a novel strategy for optical tag encoding in a single material with programmable, multi-modal photoluminescence via intrinsic and biomolecule-fluorophore association. As an example, a mixed cluster heterometallic mesoporous NdYb-based MOF was synthesized having built-in covert NIR-emitting features. The two metals crystallize in two chemically distinct homometallic hexanuclear clusters. The polynuclear, heterometallic RE-based MOF provides increased MOF functionality.

To enhance the tag's complexity, the parent MOF compound can be post-synthetically modified via a highly tunable fluorescent biomolecule labeling design strategy. The successful attachment of DNA oligos labeled with seven distinct fluorophores was demonstrated, with excitation and emission properties covering the visible spectrum (480-800 nm). This strategy allows for an expanded optical tag design via a wide range of fluorescent labels selectively added post-synthetically to create a unique signature without requiring alterations in the MOF synthesis. Furthermore, the concomitant attachment of up to three distinct fluorescently labeled oligos was confirmed in a proof-of-concept experiment. Finally, DNA inclusion as a secondary covert element was demonstrated via detection of SYBR Gold dye association. The intrinsic porosity of the MOF is deliberately preserved throughout these modifications as an additional element of the tag. This feature further enables subsequent modifications to increase the complexity of the tag via the inclusion of other functional components.

The invention provides a fast and tunable method to encode distinct information in a modular fashion to allow the rational design of an extensive library of very elaborate, difficult to counterfeit optical tags.

BRIEF DESCRIPTION OF THE DRAWINGS

The detailed description will refer to the following drawings, wherein like elements are referred to by like numbers.

FIG. 5A shows NIR photoluminescence spectra of compound 1. FIG. 5B shows lifetime decay of compound 1.

DETAILED DESCRIPTION OF THE INVENTION

Figure 1:
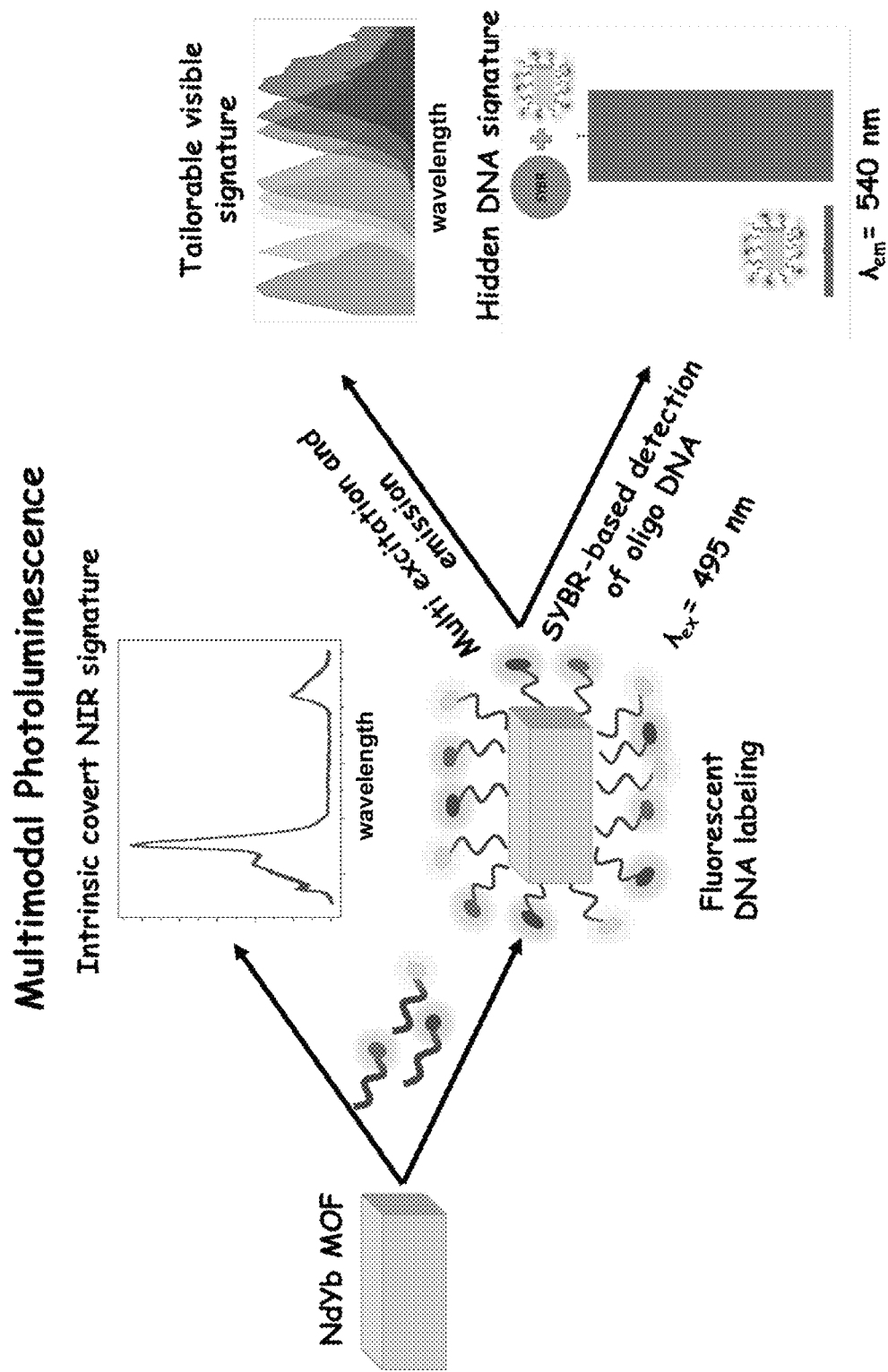
FIG. 1 is a schematic representation of a programmable, targeted approach towards multimodal photoluminescence of a mixed cluster heterometallic MOF.

The present invention expands the optical tag materials design space by accessing heterometallic MOFs using a synthetic route uniquely relevant to rare earth (RE) elements, and provides highly tunable multimodal photoluminescent signatures by implementing a post synthetic fluorescent biomolecule labeling design strategy.

The present invention is directed to an optical tag comprising a mixed cluster heterometallic metal-organic framework comprising a first rare earth-based cluster and at least one other rare earth-based cluster connected by carboxylic-acid based linkers. The first and the at least one other rare earth elements can comprise any of the lanthanides (elements 57-71, from lanthanum through lutetium) or yttrium. At least one of the first or the at least one other rare earth elements can be photoluminescent. The carboxylic-acid based linker can comprise a di-, tri-, tetra-, or hexacarboxylic acid (i.e., carboxylate). For example, the mixed cluster heterometallic MOF can comprise a ytterbium-based hexanuclear cluster and a neodymium-based hexanuclear cluster connected by tetratopic carboxylate linkers. The fluorescent biomolecule can be a phosphor-terminated nucleic acid, protein, or peptide labeled with a fluorophore.

The invention is further directed to a method to synthesize an optical tag, comprising mixing a first rare earth salt, at least one other rare earth salt, a carboxylic acid-based linker, and a modulator, in a solvent; reacting the mixture at a sufficiently high temperature and time for the mixture to form a reaction product; and cooling the reaction product to precipitate crystals of a mixed cluster heterometallic metal-organic framework comprising a first rare earth-based cluster and at least one other rare earth-based cluster connected by the carboxylic-acid based linkers. For example, the first and at least one other rare earth salts can comprise rare earth nitrates or rare earth chlorides. For example, the first rare earth salt can comprise neodymium nitrate hexahydrate and the at least one other rare earth salt can comprise ytterbium nitrate pentahydrate. The modulator can be a fluorinated simple carboxylic acid, such as a fluorobenzoic acid or fluoroacetic acid. It is postulated that the fluorinated modulator breaks apart during the synthesis and directs cluster formation, with some of the fluorine atoms bridging the metals. For example, the solvent can comprise dimethylformamide, diethylformamide, or dimethylacetamide, although many other solvents that dissolve the solutes can also be used.

Of particular interest in the context of taggant materials is the versatility in coordination chemistry of the REs with complementary features (e.g., emission properties in the NIR). As an example of the invention, a heterometallic MOF was constructed from two NIR-emitting REs: Nd, a light RE, and Yb, a heavy RE. In particular, Nd has the tendency to accommodate higher coordination numbers, and has been shown to promote structural diversity and high nuclearity clusters. See G. Zucchi et al., *Inorg. Chem.* 47, 10398 (2008); and K. Su et al., *CrystEngComm* 18, 4921 (2016). Furthermore, Nd to Yb energy transfer is anticipated when directly exciting Nd ions at 808 nm. See J. I. Deneff et al., *Angew. Chem. Int. Ed.* 60, 1203 (2021); D. F. Sava Gallis et al., *ACS Appl. Mater. Interfaces* 9, 22268 (2017); and D. F. Sava Gallis et al., *CrystEngComm* 20, 5919 (2018). Accordingly, a hierarchically complex MOF was achieved under unique synthetic conditions. In this material, the Nd and Yb metal ions are segregated in two chemically distinct hexanuclear clusters. The Nd-based cluster consists of two staggered $\mu_3$-oxo Nd trimers bridged together by four $\mu_3$-OH groups, while the Yb-based cluster adopts the default hexanuclear cluster arrangement.

To further expand the photoluminescent properties of this exemplary system as relevant to highly intricate anti-counterfeiting optical tags, this novel MOF was used as the base for a fluorescent biomolecule labeling system. A graphical representation highlighting the hierarchical complexity towards multimodal photoluminescence is depicted in FIG. 1, and will be described more fully below.

Fluorescently labeled DNA oligos are available commercially with a wide range of fluorophores, allowing tailoring of the visible tag signature with one, two, or more visual signatures. Furthermore, the DNA can act as a secondary covert signature that can be detected using dyes with high affinity for DNA. DNA oligo MOF complexes have previously been used for detection of viruses and cellular delivery. See Y. Wang et al., *Biosens. Bioelectron.* 169, 112604 (2020); F. Wu et al., *Luminescence* 35, 440 (2020); and J. Zhuang et al., *Small* 13, 1700880 (2017). DNA association with MOFs has been demonstrated using click chemistry, carbodiimide chemistry, and passive association with the DNA backbone or with phosphate terminators added to oligos. See W. Morris et al., *J. Am. Chem. Soc.* 136, 7261 (2014); J. S. Kahn et al., *Adv. Mater.* 29, 1602782 (2017); W. Ning et al., *Small* 14, 1703812 (2018); Z. Wang et al., *J. Am. Chem. Soc.* 139, 15784 (2017); S. Wang et al., *J. Am. Chem. Soc.* 139, 9827 (2017); and S. Wang et al., *J. Am. Chem. Soc.* 141, 2215 (2019).

The present invention provides a rapid and tailorable way to encrypt distinct information in a modular fashion via post-synthetical attachment of a variety of distinct fluorophores, with excitation and emission properties across a wide range of the visible spectrum (e.g., 480-800 nm). Furthermore, the simultaneous addition of multiple fluorescently labeled biological molecules is possible, to serve as a rapid and tailorable way to enhance the complexity via multimodal emission properties.

The exemplary heteronuclear MOF (compound 1) was synthesized by a solvothermal reaction. A reaction mixture containing neodymium nitrate hexahydrate ($Nd(NO_3)_3 \cdot 6H_2O$; 5 mg, 0.011 mmol), ytterbium nitrate pentahydrate ($Yb(NO_3)_3 \cdot 5H_2O$; 5.15 mg, 0.011 mmol), a tetratopic organic linker 1,2,4,5-tetrakis (4-carboxylphenyl) benzene (TCPB, 3.7 mg, 0.0066 mmol), 2-fluorobenzoic acid (FBA, 575 mg, 4.10 mmol) as a modulator, and the solvent N,N'-dimethylformamide (DMF 3.0 mL) was placed in a 20 mL scintillation vial and heated to 115° C. at 1.5° C./min, held at 115° C. for 18 hours, and then cooled to room temperature at 1.5° C./min. The resulting hexagonal prism-like crystals were washed three times with an excess of DMF and three times with an excess of methanol before being suspended in methanol.

Figure 2A:
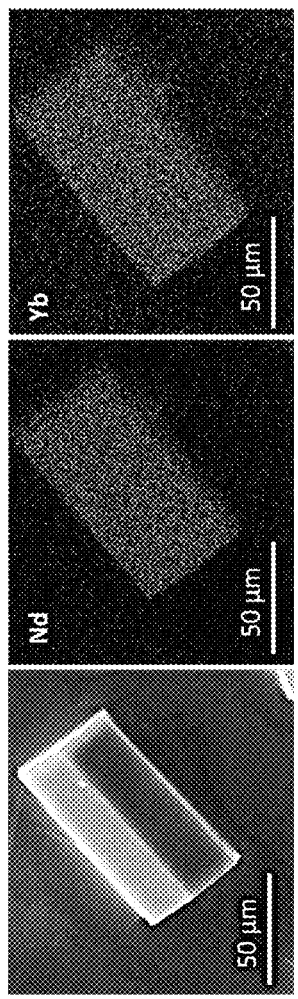
FIG. 2A is an SEM image of single crystal of YbNdTCPB (compound 1) and corresponding EDS maps for Nd and Yb metal ions.
Figure 2B:
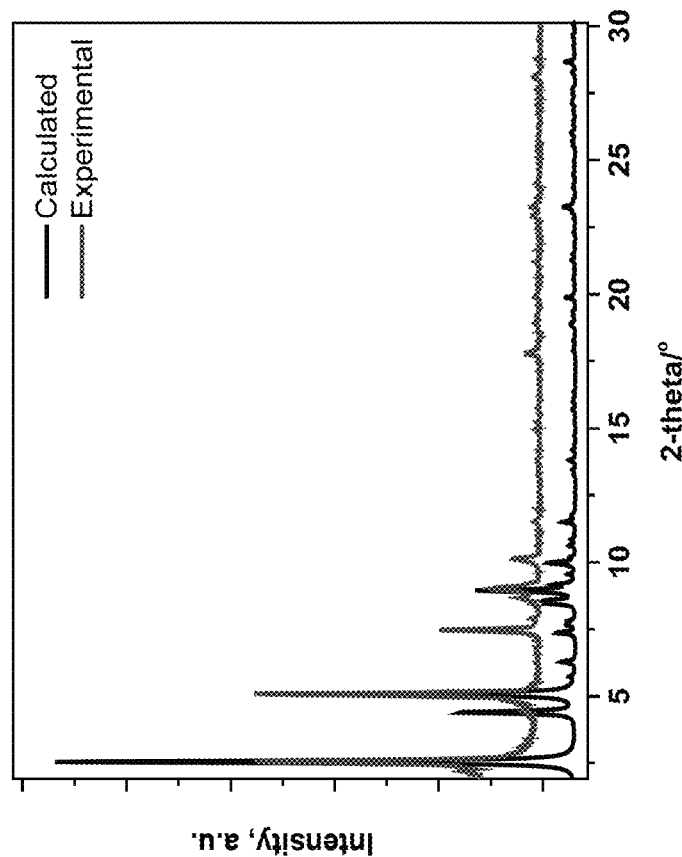
FIG. 2B shows calculated and experimental PXRD patterns of compound 1.

The resulting single crystals had hexagonal prism morphology, as shown by the scanning electron microscope (SEM) and corresponding energy dispersive spectroscopy (EDS) images in FIG. 2A. Elemental mapping on a representative compound 1 individual single crystal indicates a very homogeneous distribution of both Nd and Yb. Powder X-ray diffraction (PXRD) patterns of the bulk sample, as shown in FIG. 2B, reveal a very good correlation between the calculated and experimental data, confirming the phase purity of the as-synthesized material. To be noted, the experimental PXRD pattern suffers from a preferred orientation effect, which amplifies intensity for the a-axis reflections. This is evidenced by the two strongest peaks in the pattern, which correspond to the (100) and (200) reflections. The (101) reflection is tilted significantly away from the diffraction condition (i.e., >30) and therefore is suppressed in the experimental pattern.

Figure 3:
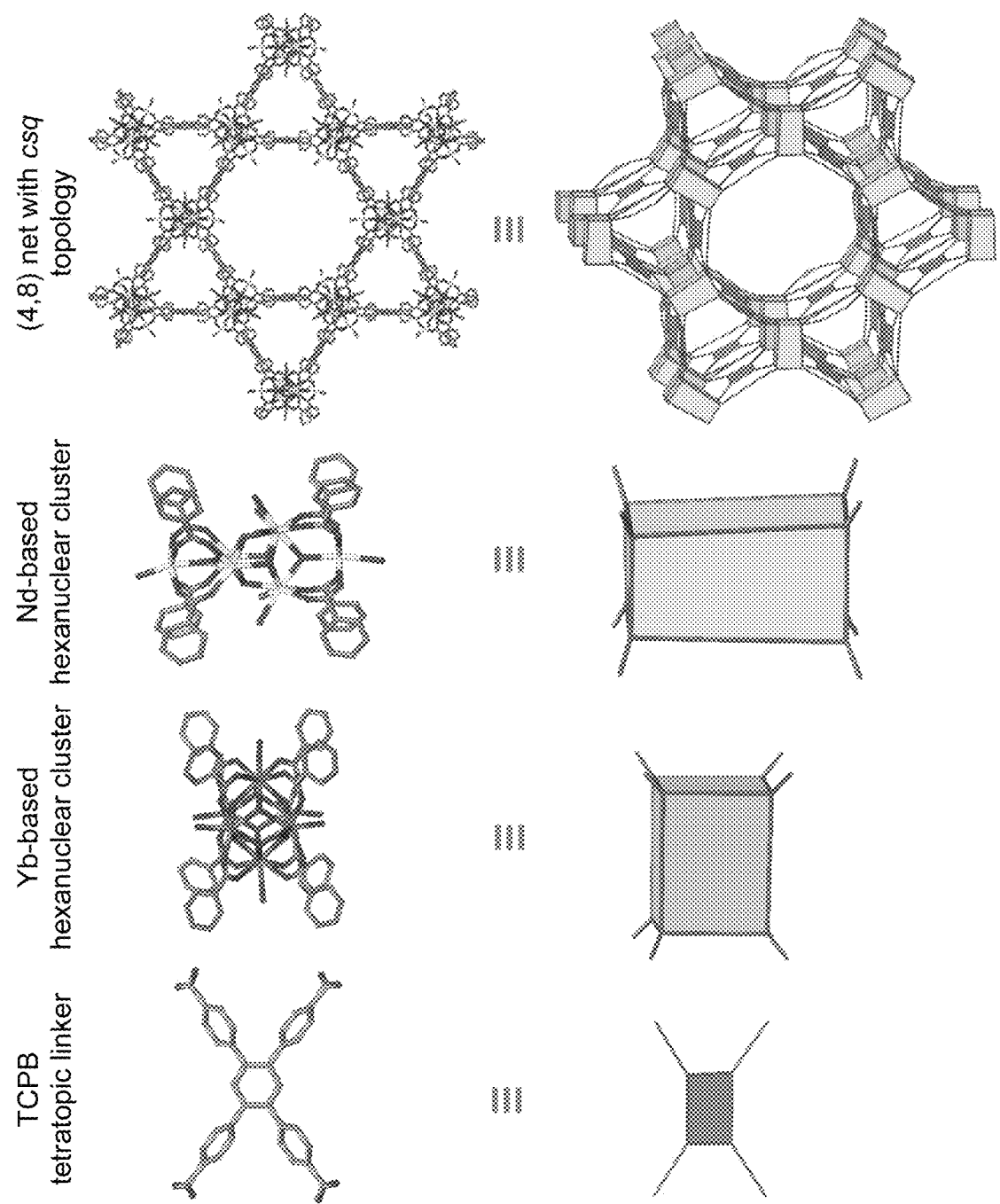
FIG. 3 illustrates ball-and-stick representations of a TCPB linker; Yb-based hexanuclear cluster; Nd-based hexanuclear cluster; and a representative framework structure highlighting triangular and hexagonal porous channels. Atom color scheme: C=grey; O=red; Yb=dark green; Nd=light green. H atoms were omitted for clarity. The bottom row illustrates corresponding geometrical representations for each of the molecular building blocks depicted on the top row: TCPB viewed as a 4-connected node; Yb-based cluster depicted as 8 connected nodes; Nd-based cluster depicted as 8 connected nodes; and the resulting (4,8) net with csq topology.

To gather molecular level insights into distinct structural features and the spatial arrangement of each of the individual metals, X-ray single-crystal diffraction studies were conducted. Single-crystal studies focused on deciphering the precise metal partitioning in heterometallic MOFs are not trivial, especially when the metals have similar electron densities. See Q. Liu et al., *J. Am. Chem. Soc.* 138, 13822 (2016); and Z. Ji et al., *Science* 369, 674 (2020). As a result of these studies, compound 1 was formulated as $\{[(Yb_6(\mu_3\text{-OH}-)_8(H_2O)_4(OH-)_2][(Nd_6(\mu_3\text{-OH}-)_4(\mu_3\text{-O})_2(H_2O)_6(OH-)_2]\}(TCPB)_4$. The material crystallizes in the P3 space group and consists of two distinct polynuclear metal clusters, namely an ordered Yb-based hexanuclear cluster and a disordered Nd-based hexanuclear cluster connected by the TCPB organic linkers, as shown in FIG. 3.

In the crystal structure of compound 1, the ordered hexanuclear Yb-based cluster adopts a well characterized coordination previously observed in a series of RE-based MOFs. See D.-X. Xue et al., *J. Am. Chem. Soc.* 135, 7660 (2013); D. F. Sava Gallis et al., *ACS Appl. Mater. Interfaces* 9, 22268 (2017); R. Luebke et al., *Chem. Sci.* 6, 4095 (2015); D. F. Sava Gallis et al., *ACS Appl. Mater. Interfaces* 11, 43270 (2019); and K. S. Butler et al., *ACS Appl. Mater. Interfaces* 12, 31217 (2020). Within the hexanuclear cluster, four Yb metal centers are 8-coordinated and two display a 9-connected coordination geometry. The metals are bridged by eight independent TCPB linkers, four on the top and four on the bottom of the cluster, eight $\mu_3$-OH groups and two equatorial OH groups. The remaining coordination sites are occupied by water molecules.

The Nd-based hexanuclear cluster consists of two $\mu_3$-oxo Nd trimers in a staggered configuration, bridged together by four $\mu_3$-OH groups, and further extended by eight independent TCPB linkers. The cluster is disordered where the alternate orientation is generated by a 180° rotation of the Nd-based cluster about the c-axis direction, thus inverting the apical positions of the cluster with respect to the orientation shown in FIG. 3.

Notably, this is believed to be the first occurrence of this novel complex cluster in a MOF. Further, this is the first documented occurrence of a RE-based hexanuclear cluster adopting this unique configuration. It has been previously reported as a discrete cluster, primarily with Fe and in an extended one-dimensional coordination polymer. See W. Micklitz and S. J. Lippard, *Inorg. Chem.* 27, 3067 (1988); M. A. Ehsan et al., *Inorganica Chim. Acta* 376, 189 (2011); and S. G. Baca et al., *Inorg. Chem.* 52, 4154 (2013).

The arrangement of each of the individual molecular building blocks gives rise to a three periodic mesoporous structure, with triangular channels of 11.9 Å and hexagonal channels of 26.7 Å in diameter, as shown in FIG. 3. The channels propagate along the c-axis direction with alternating layers composed of one type of the two possible metal clusters. From a topological perspective, the TCPB linker acts as a 4-connected extension point, and the two hexanuclear clusters are depicted as 8-connected nodes, as illustrated by the corresponding geometrical figures shown in the bottom row of FIG. 3. Interestingly, although this material is based on two structurally distinct 8-connected nodes corresponding to each of the independent Yb and Nd ions, the two nodes are topologically equivalent. This results in a net with (4,8) connectivity, corresponding to a csq topology, previously reported in a series of Zr-based MOFs. See W. Morris et al., *Inorg. Chem.* 51, 6443 (2012); D. Feng et al., *Angew. Chem. Int. Ed.* 51, 10307 (2012); J. E. Mondloch et al., *J. Am. Chem. Soc.* 135, 10294 (2013); and P. Li et al., *Chem* 4, 1022 (2018).

Figure 4:
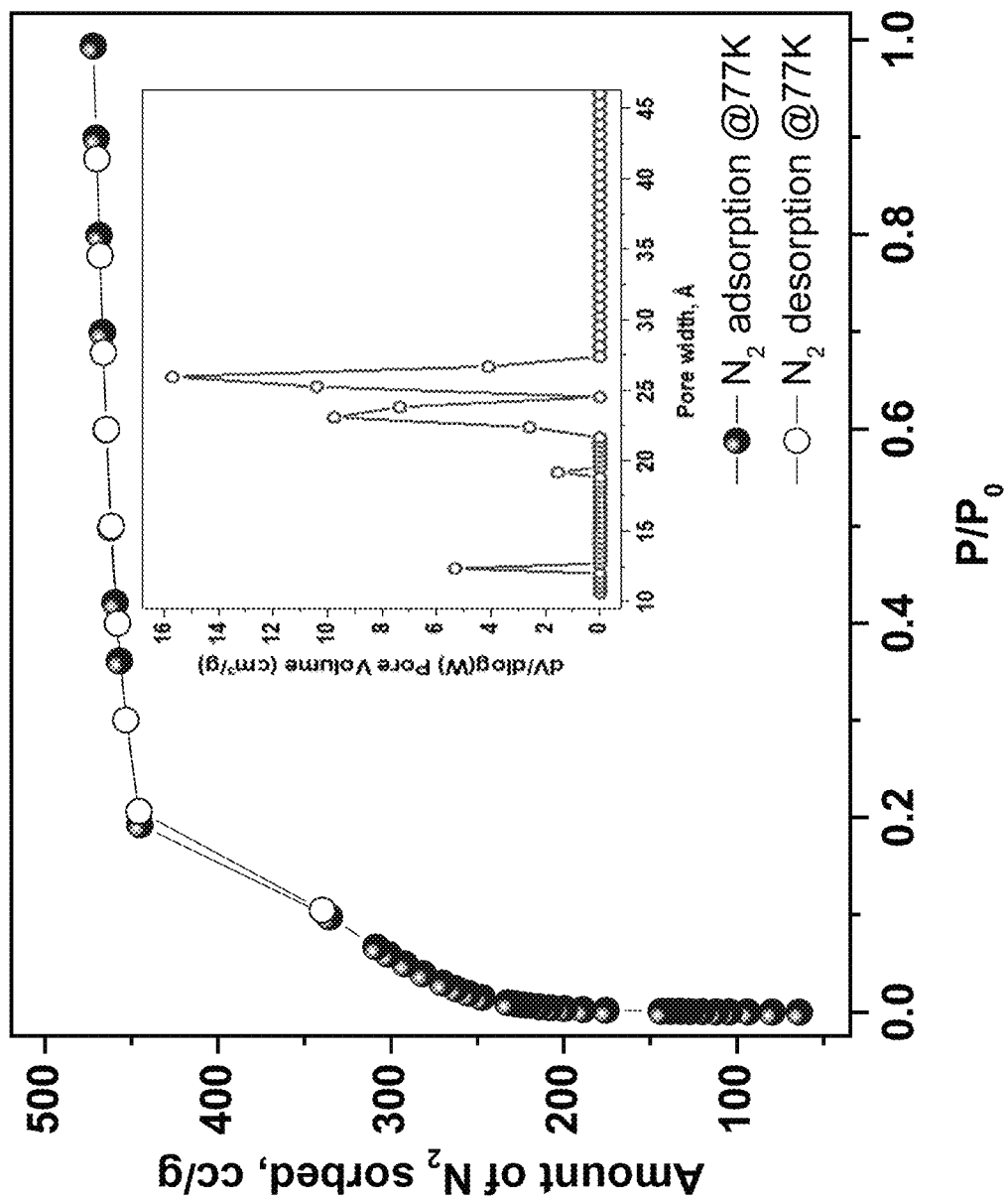
FIG. 4 is a graph of nitrogen adsorption isotherms measured at 77 K of compound 1.

As mentioned above, the crystal structure of compound 1 reveals the potential for accessible mesoporosity as facilitated by the large porous channels along the c-axis. Accordingly, the permanent porosity was investigated by measuring the nitrogen adsorption isotherm at 77 K on the methanol exchanged and desolvated compound 1, as shown in FIG. 4. The material displays an isotherm that best resembles the IVc type, with a pronounced knee noted in the 0.05 to 0.2 P/Po pressure range, associated with the filling of mesoporous cages. The surface area was found to be 1426 m$^2$/g using the Brunauer-Emmett-Teller (BET) method. Pore size distribution was calculated using a density functional theory (DFT) model (inset, FIG. 4) highlighting contributions from both the smaller triangular micropores (~12 Å) and the larger hexagonal mesoporous channels (~27 Å). These values are in good agreement with those determined by single-crystal X-ray diffraction analyses.

The NIR photoluminescence (PL) properties in compound 1 were also investigated. When directly exciting the Nd metal ions at 808 nm, the characteristics emission peaks for Nd$^{3+}$ at ~1325 nm ($^4F_{3/2}$-$^4I_{13/2}$ transitions) and ~1060 nm, ($^4F_{3/2}$-$^4I_{11/2}$ transitions) were observed, as shown in FIG. 5A. Additionally, Yb$^{3+}$ emission at ~980 and 1025 nm ($^5F_{5/2}$→$^2F_{7/2}$ transition) was noted, as a result of Nd to Yb nonradiative energy transfer from the $^4F_{5/2}$ energy level of Nd$^{3+}$ to the $^5F_{5/2}$ energy level of Yb$^{3+}$. Decay dynamics were monitored via time-domain PL lifetime measurements by direct excitation of the TCPB ligand using a pulsed 337 nm N$_2$ laser. As shown in FIG. 5B, the lifetime displayed the characteristic biexponential decay previously observed in NdYb-based samples of T$_1$=0.69 μs and T$_2$=3 ρs. See J. I. Deneff et al., *Angew. Chem. Int. Ed.* 60, 1203 (2021).

Following examination of the structural properties of compound 1, the ability of this heterometallic MOF to act as a base for DNA attachment via phosphate termination of the DNA oligo was assessed. The use of secondary labeling with biomolecules provides a unique, tailored fluorescent label addition without the need to modify the synthesis for each individual color desired and the ability to create controlled, multimodal emission in a single material.

Phosphate-terminated oligos have previously been demonstrated as a facile way to associate DNA oligos with a variety of MOFs. See S. Wang et al., *J. Am. Chem. Soc.* 139, 9827 (2017); and S. Wang et al., *J. Am. Chem. Soc.* 141, 2215 (2019). The terminal phosphate-modified DNA oligos interact with the coordinatively unsaturated metal sites on the MOF surface, facilitating dense surface functionalization with DNA oligos. See S. Wang et al., *J. Am. Chem. Soc.* 139, 9827 (2017). To functionalize the YbNdTCPB MOF (compound 1) with the DNA oligos, 80 μg of compound 1 in methanol was washed twice via centrifugation with molecular biology grade water to remove residual alcohol. Compound 1 was then resuspended in 50 μg of molecular biology grade water. To the resuspended compound 1, 20 μL of 100 μM DNA oligo in nuclease free water was added. For mock functionalization, 20 μL of nuclease free water without oligo was used. Compound 1 was then incubated for 4 hours at room temperature using a rotary tube mixer. To remove unbound oligo, compound 1 was washed twice with nuclease-free water via centrifugation. Samples were resuspended in nuclease-free water. All oligos shared the same sequence 5' fluorophore TGG TGG TGG TGG TGG TGG TGG TGG TGG TGG T terminal phosphate group 3'.

To allow direct visualization and quantification of DNA oligo attachment, a phospho-terminated DNA oligo labeled with the fluorophore TAMRA was used as an example. See S. Wang et al., *J. Am. Chem. Soc.* 141, 2215 (2019). When assessed for fluorescence, compound 1 shows no fluorescent signature in the expected range of the TAMRA fluorophore. However, when the TAMRA-labeled DNA oligo is attached, significant fluorescence is present with both lamp and laser-based excitation on DNA oligo-associated compound 1. Spectral analysis using the lambda scan feature on a confocal microscope demonstrates the fluorescent signature expected from the TAMRA molecule is present on compound 1. By comparing the intensity of the fluorescent signal to a standard curve of the phospho-TAMRA oligo, it was determined that 0.035 nmol of oligo was attached per 100 μg of compound 1. This quantification may underestimate the amount of oligo present on compound 1, as a number of MOFs have shown quenching of fluorescent tags present on oligos. See Y. Wang et al., *Biosens. Bioelectron.* 169, 112604 (2020); and F. Wu et al., *Luminescence* 35, 440 (2020). However, even if minimal quenching is occurring, the signal present on compound 1 is readily bright enough to visualize.

Figure 6B:
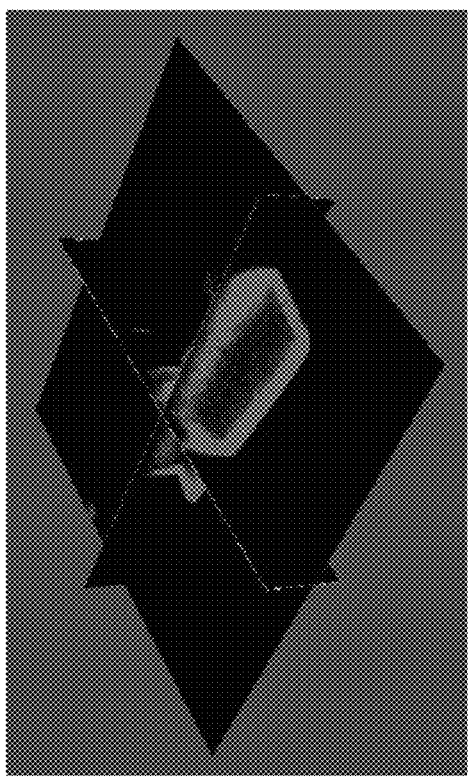
FIG. 6B is a 3D reconstruction of z-stack images of compound 1 with TAMRA-labeled DNA showing surface association of DNA oligo.
Figure 6A:
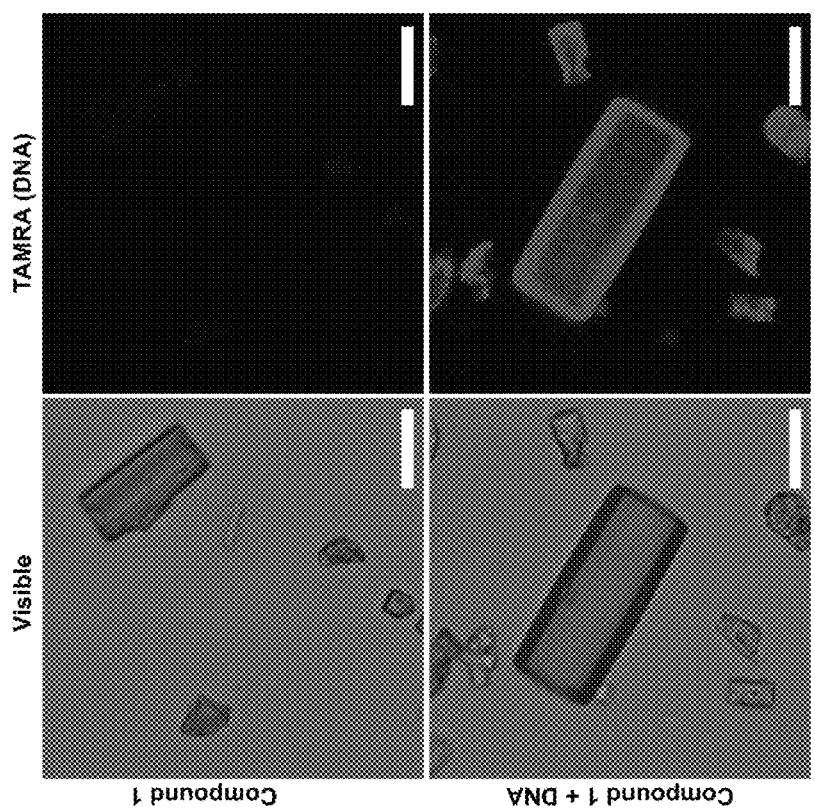
FIG. 6A shows representative confocal images of compound 1 with and without TAMRA-labeled DNA. Scale bar 25 μm.

Next, the potential to directly image the phospho-TAMRA oligo on compound 1 was evaluated. Microscopic examination showed compound 1 was easily visible using light microscopy, but showed no fluorescent signature when illuminated with the 552 nm laser in the absence of the TAMRA DNA oligo. The addition of the phospho-TAMRA DNA oligo resulted in a strong fluorescent signature on compound 1, as shown in FIG. 6A. The visible association of the phospho-TAMRA oligo on the surface of the MOF is similar to previous observations of this oligo on the surface of NU-1000 and further demonstrates the versatility of this attachment methodology. See S. Wang et al., *J. Am. Chem. Soc.* 141, 2215 (2019). To determine if the oligo was able to access the internal volume of the compound 1 crystal, a series of confocal images in the Z-plane were taken. This z-stack was then reconstructed to create a 3D image of the MOF, shown in FIG. 6B. The 3D reconstruction demonstrated that the oligo is surface associated and does not access the interior of compound 1. Given the pore size of compound 1, the surface association was expected and leaves open the possibility of using the internal structure of the MOF for the inclusion of other signature molecules.

Figure 7:
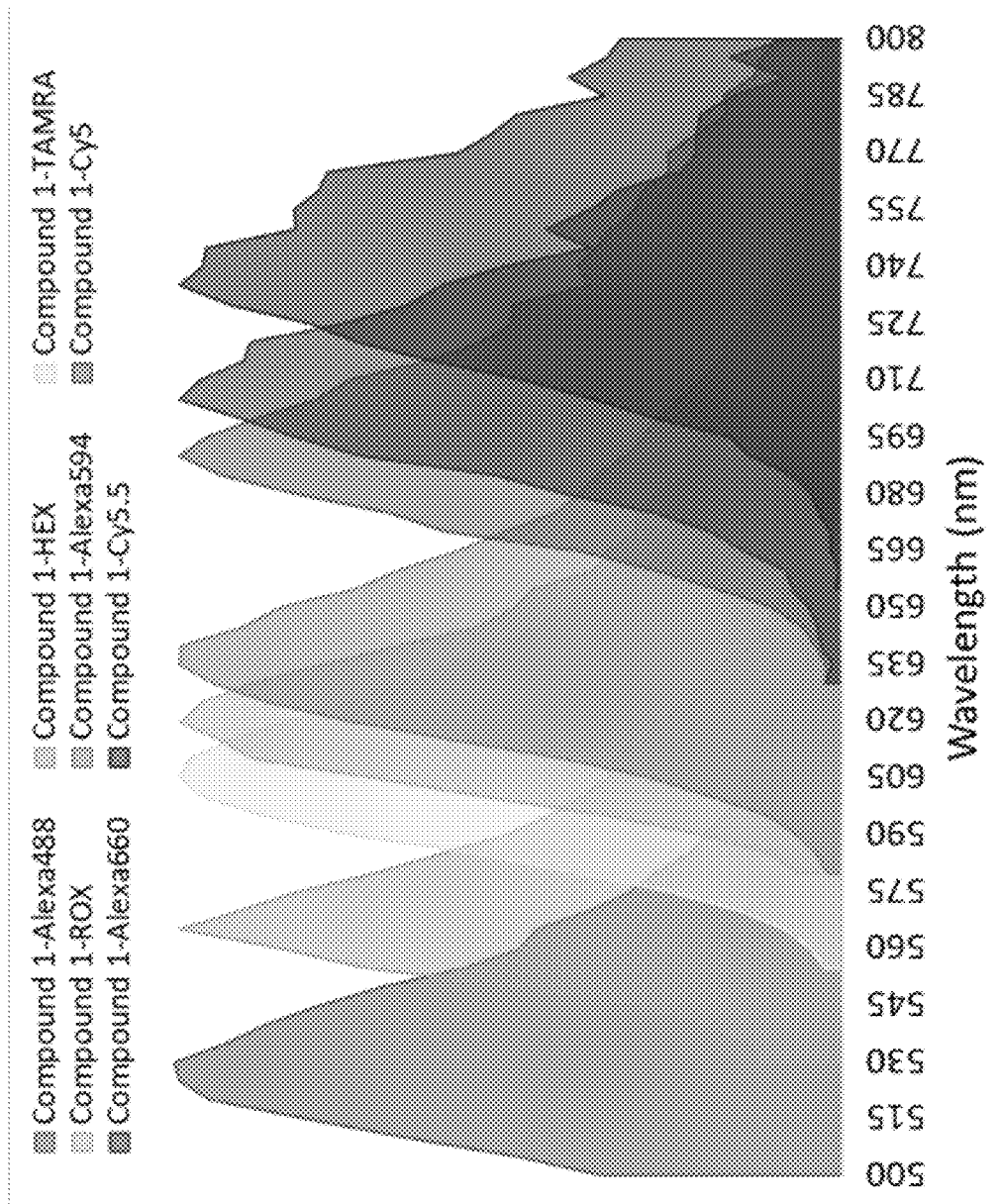
FIG. 7 shows spectral scans of compound 1 labeled with individual fluorescently labeled DNA oligos.

The ability to readily associate the phospho-tagged oligo to compound 1 raises the potential to use fluorescently tagged biological molecules as a post-synthetic functionalization approach to add optical complexity. An advantage of this strategy over direct incorporation during synthesis is that the phospho-tagged oligo can be commercially synthesized with a wide range of fluorescent labels and selectively added via post-synthetic modification to create a unique signature without requiring alterations in the MOF synthesis. To test this possibility, seven additional fluorophores (Alexa 488, Alexa 594, Alexa 660, HEX, ROX, Cy5 and Cy5.5) that covered the wide range of commercially available fluorophores were selected for oligo inclusion. These oligos with alternate fluorescent labels were individually attached to compound 1 and the spectra of each label on the MOF was assessed, as shown in FIG. 7. The spectral scans showed the ability to detect each fluorescently labeled DNA oligo on compound 1 and the retention of spectral separation of the fluorescent labels associated with compound 1.

Following the determination of spectral separation, the ability to detect the fluorescent oligo on the MOF surface using set excitation and emission was evaluated. In each case, the compound 1 alone had little to no detectable signal at the excitations and emissions set for the attached fluorophores. This was expected as Yb and Nd emit in the NIR rather than the visible range. Additionally, while the linker does emit in the visible range, the excitation and emission spectra do not overlap with the fluorophores selected.

Detection via microplate reader confirmed that all of the fluorescently labelled oligos were successfully attached and detectable on compound 1. The feasibility to use the microplate reader to validate the identity of the fluorescent oligo is very important in the context of implementing low-cost, easily accessible, standard laboratory equipment. Although all the fluorescent oligo-labeled compound 1 samples were successfully detected, the intensity of the signal varied. In general, the labels with emission range of 520-620 nm were stronger than those in the range above 680 nm.

Figure 8:
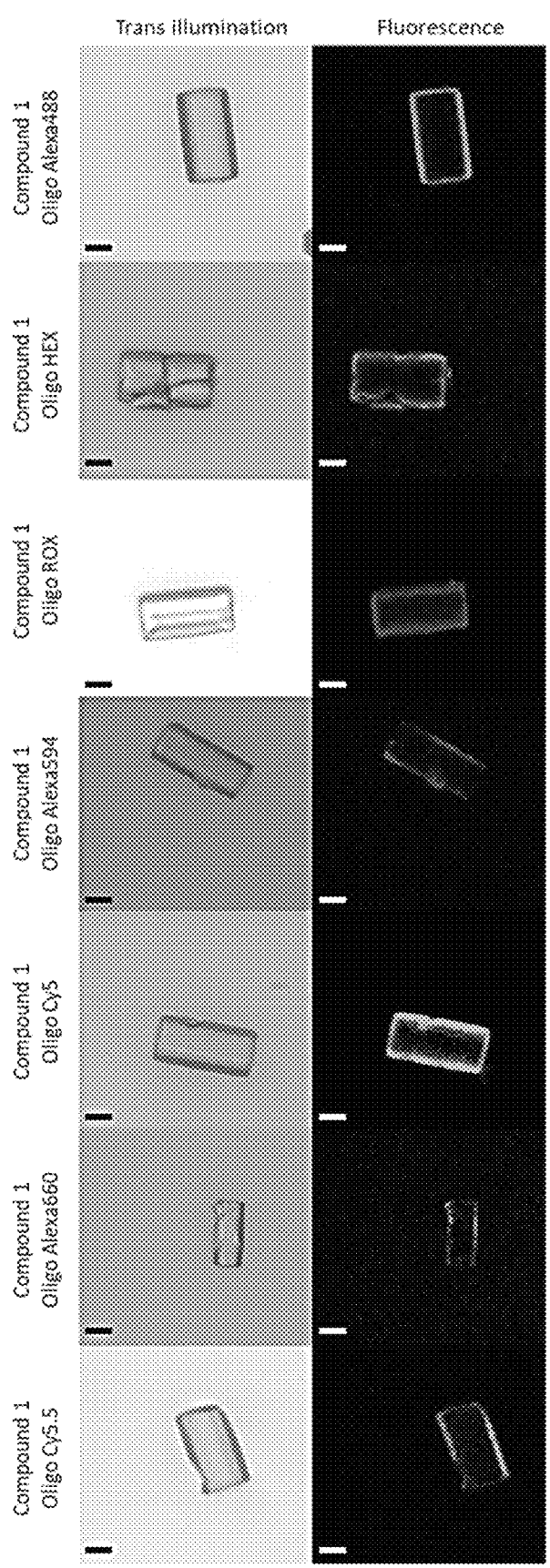
FIG. 8 shows confocal microscopy images of compound 1 with and without fluorescent labeled DNA oligos visualized by transillumination and fluorescence. Fluorescent images are color coded to identify the laser used for fluorescent visualization, 488 nm (green), 552 nm (red) and 638 nm (turquoise). Scale bar 20 μm.

Following confirmation of oligo attachment regardless of fluorescent label, the ability to visualize these labels on the surface of compound 1 via microscopy was assessed. As shown in FIG. 8, all seven additional fluorophore-labeled oligos were visible on the surface of compound 1. Similar to the previous imaging of the TAMRA-labeled DNA oligo shown in FIGS. 6A and 6B, the labeling with the new oligos is surface associated, resulting in strong labeling along the edges of compound 1 when imaged via confocal microscopy. The intensity of the signal varied among various fluorophores. This variation was expected as the lasers have different efficiencies in excitation of the various fluorophores. For example, the 488 nm laser is more efficient at exciting Alexa488 than HEX and the 638 nm laser is more efficient at exciting Cy5 than Cy5.5. Although the efficiency of excitation may account for some of the variability in signal, it does not account for all of it. The fluorophores have known differences in brightness that are also visible. For example, Cy5 and Alexa660 have the same efficiency for excitation with the 638 nm laser, but Cy5 is known to be brighter than Alexa660. A wide variety of fluorescent labels are commercially available and could be attached to the phosphor-terminated oligo to allow tailoring to both the detection system and the desired signal brightness.

Figure 9:
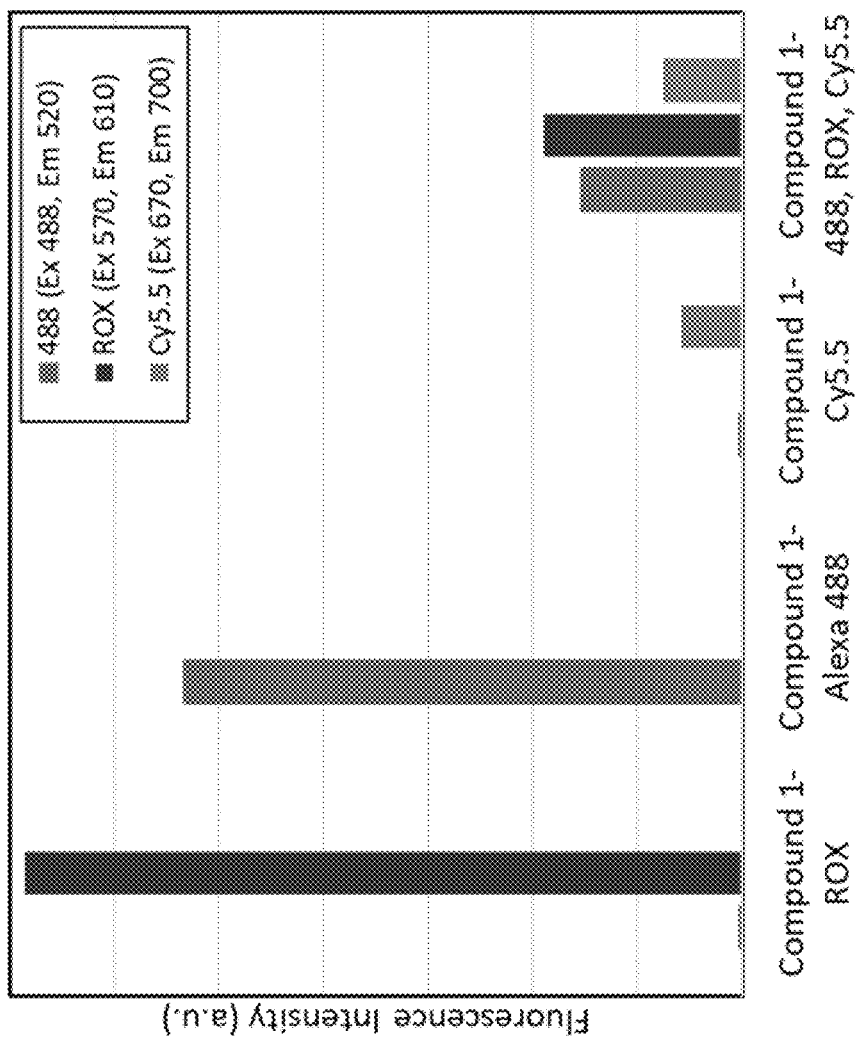
FIG. 9 shows detection of single and tri-labeling of compound 1 with fluorescent oligos for the first design. Detection was done using a microplate reader, samples were assessed for each potential fluorophore (Alexa488, ROX and Cy5.5), the excitation and emission settings for each are displayed in the legend.

Next, the potential to design a complex, multimodal emission signature via concomitant labeling of three distinct fluorescent oligos to compound 1 was explored. Two different designs were created that each utilized three fluorescent oligos. These designs were chosen to allow the specific detection of a single fluorescent signal on each laser. Single- and tri-labeled compound 1 samples based on the tri-labeled first design were created for comparison. The samples were first examined by microplate reader, as shown in FIG. 9. All of the single-labeled compound 1 samples showed little to no background signal in the other channels. The signals from the ROX and Alexa488 oligos were stronger than the Cy5.5 signal, but all signals were readily detectable. When all three labels were attached to compound 1 simultaneously, all of the three signals were readily detectable within the same sample.

Following the success with the first design, the matched single and tri-labeled compound 1 samples for a tri-labeled second design were created. Similar to the first design, each of the three single-label samples showed little to no signal in the alternate channels, and the tri-labeled compound 1 clearly showed all three fluorescently labeled oligos were present within a single sample.

Figure 10:
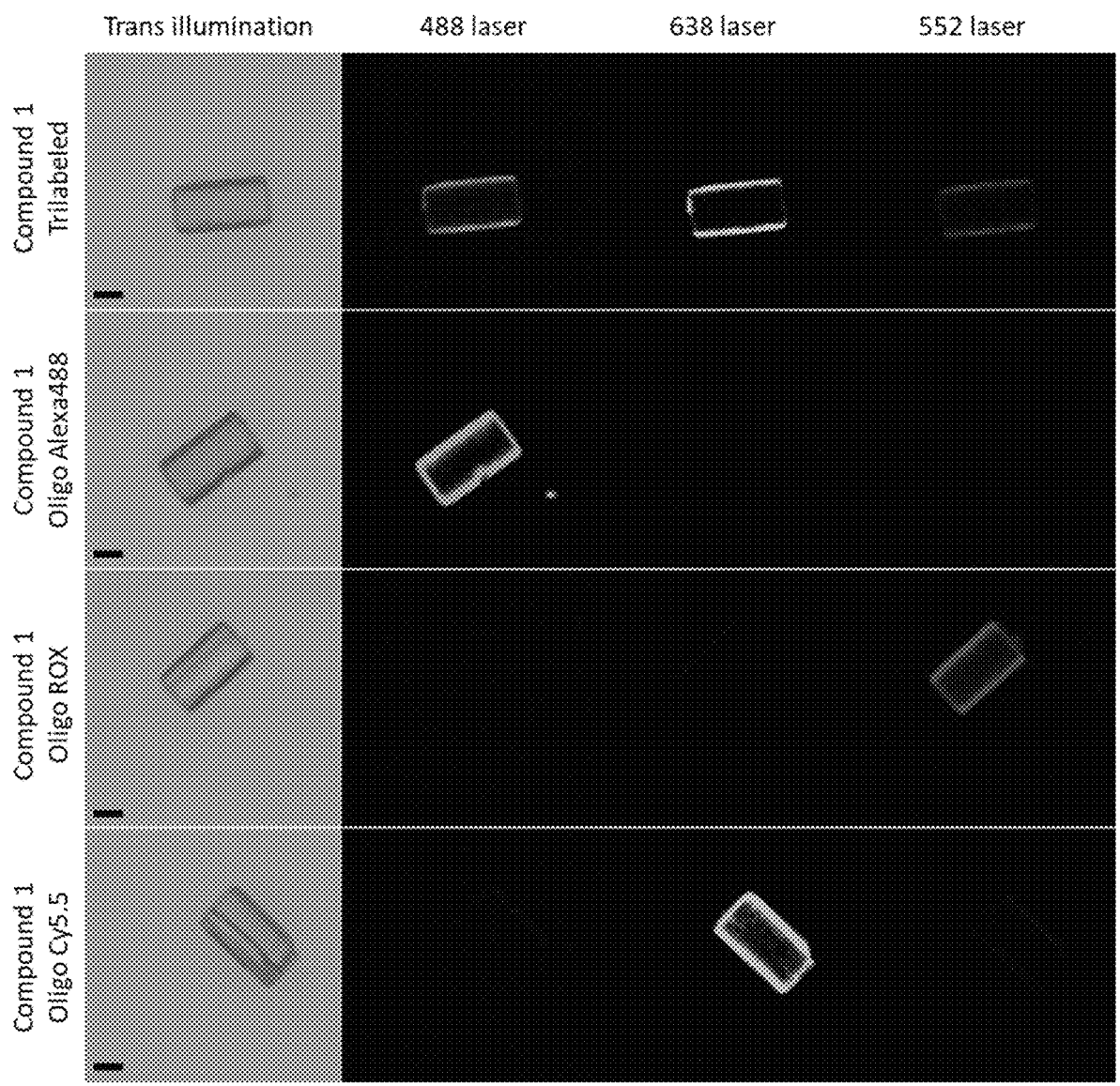
FIG. 10 shows confocal microscopy images of compound 1 with single or triple fluorescent labeled DNA oligos (first design) visualized by transillumination and fluorescence. Fluorescent images are color coded to identify the laser used for fluorescent visualization, 488 nm (green), 552 nm (red) and 638 nm (turquoise). Scale bar 20 μm.

Following confirmation that the tri-labeled compound 1 samples were triply labeled and that the signals could be differentiated, these samples were imaged via confocal microscopy. The visualization of the tri-labeled first design and matched single-labeled samples demonstrates selective visualization of all three labels within the same sample, as shown in FIG. 10. Comparison with the matched single-labeled samples shows no cross talk between the channels and demonstrates the specificity of the detection. To determine if other fluorophore combinations could also be utilized, the tri-labeled second design sample was also examined via confocal microscopy. Similar to the first design samples, all three fluorophores could be distinctly identified within the same sample.

Figure 11:
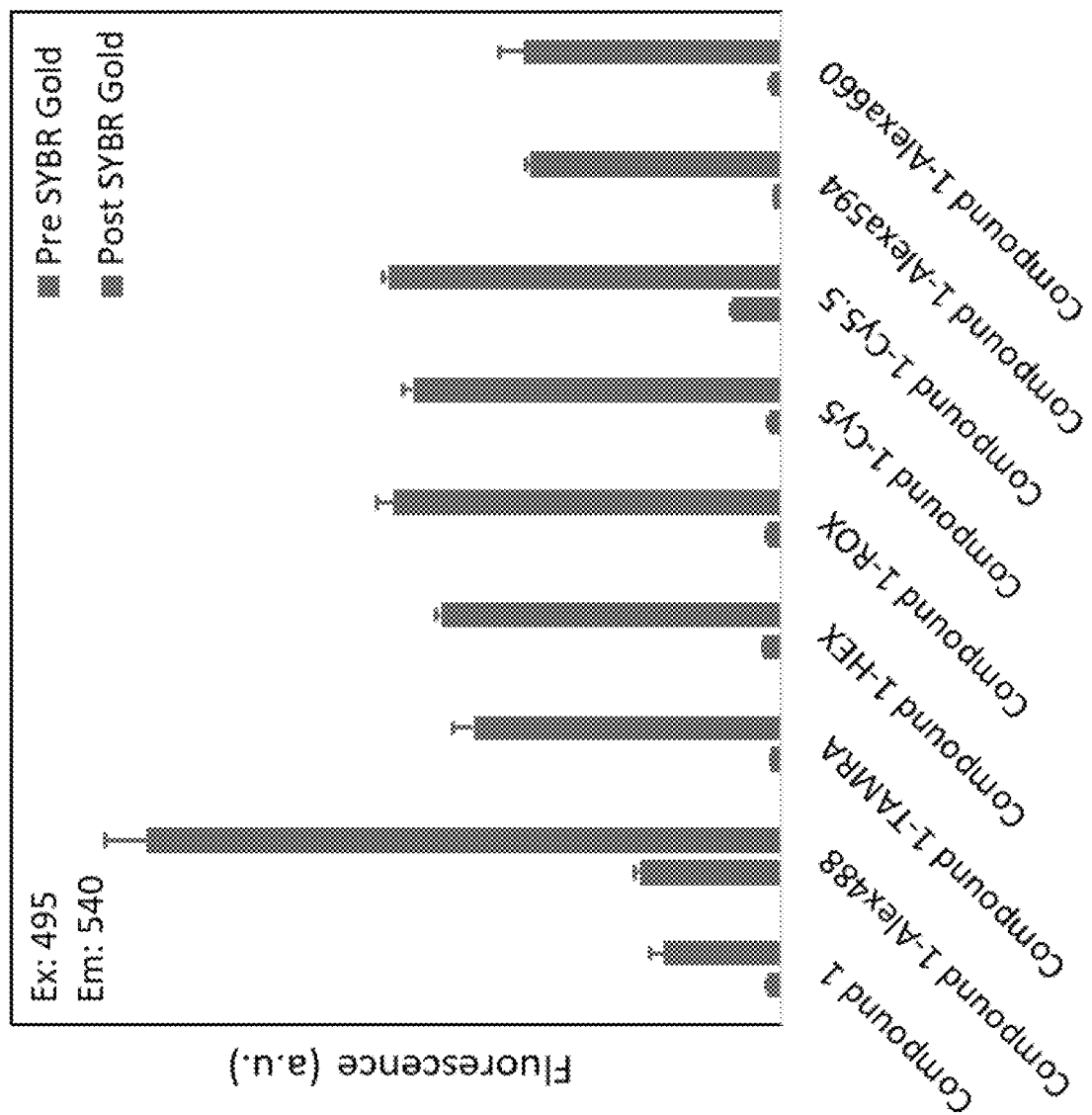
FIG. 11 is a graph of detection of oligo DNA on compound 1 with SYBR Gold. Detection was done using a microplate reader with excitation of 495 nm and emission of 540 nm.

Finally, to further demonstrate the DNA inclusion as a secondary covert element in the multifunctional optical tag, the potential to visualize its presence via targeted dye interaction was evaluated. DNA labeled with the interacting dye, SYBR Green I, has previously been proposed as a method to create tags via labeled DNA stabilized with silica. See W. Morris et al., *Inorg. Chem.* 51, 6443 (2012). As the DNA itself was not intended to act as the visible element in this system, whether the DNA could be identified in the full complex via post labeling rather than prelabeled was tested. SYBR Gold is an unsymmetrical cyanine dye that can be used as a stain for nucleic acids. The addition of SYBR Gold to oligo-labeled compound 1 resulted in in a significant fluorescent signature in the presence of oligo DNA, as shown in FIG. 11. Interestingly, examination of compound 1 labeled with Alexa 488 oligo demonstrated the potential to detect the DNA, even in the presence of a fluorophore with an overlapping signature. The post labeling of the DNA demonstrates the potential to use DNA detection as an additional confirmation methodology for the complex tag system described herein.

The present invention has been described as a mixed cluster heterometallic metal-organic framework for complex optical tags. It will be understood that the above description is merely illustrative of the applications of the principles of the present invention, the scope of which is to be determined by the claims viewed in light of the specification. Other variants and modifications of the invention will be apparent to those of skill in the art.

We claim:
1. A method for synthesizing an optical tag, comprising:
mixing a first rare earth salt, at least one other salt of a different rare earth, a carboxylic acid-based linker, and a modulator, in a solvent;
reacting the mixture at a sufficiently high temperature and time for the mixture to form a reaction product; and
cooling the reaction product to precipitate crystals of a mixed cluster heterometallic metal-organic framework comprising a first rare earth-based cluster and at least one other chemically distinct rare earth-based cluster connected by the carboxylic-acid based linkers.

2. The method of claim 1, wherein the first rare earth salt and the at least one other salt of a different rare earth comprises a rare earth nitrate or rare earth chloride.

3. The method of claim 2, wherein the first rare earth salt comprises neodymium nitrate hexahydrate, the at least one other salt of a different rare earth comprises ytterbium nitrate pentahydrate, the first rare earth-based cluster comprises a ytterbium-based hexanuclear cluster and the at least one other chemically distinct rare earth-based cluster comprises a neodymium-based hexanuclear cluster.

4. The method of claim 1, wherein the carboxylic-acid based linker comprises a di-, tri-, tetra-, or hexacarboxylic acid.

5. The method of claim 4, wherein the carboxylic-acid based linker comprises 1,2,4,5-tetrakis (4-carboxylphenyl) benzene.

6. The method of claim 1, wherein the modulator comprises a fluorinated carboxylic acid.

7. The method of claim 6, wherein the fluorinated carboxylic acid comprises a fluorobenzoic acid or a fluoroacetic acid.

8. The method of claim 1, wherein the solvent comprises dimethylformamide, diethylformamide, or dimethylacetamide.

9. The method of claim 1, wherein at least one of the first rare earth-based cluster or the at least one other chemically distinct rare earth-based cluster is photoluminescent.

10. The method of claim 1, further comprising functionalizing a surface of the mixed cluster heterometallic metal-organic framework with one or more phospho-terminated biological molecules.

11. The method of claim 10, wherein the one or more phospho-terminated biological molecules comprises a nucleic acid, protein, or peptide.

12. The method of claim 10, wherein the one or more phospho-terminated biological molecules is labeled with one or more fluorophores.

13. The method of claim 11, further comprising labeling the nucleic acid-functionalized mixed cluster heterometallic metal-organic framework with a dye.

14. The method of claim 13, wherein the dye comprises SYBR Gold dye.

15. An optical tag comprising a mixed cluster heterometallic metal-organic framework comprising a first rare earth-based cluster and at least one other chemically distinct rare earth-based cluster connected by a carboxylic-acid based linker.

16. The optical tag of claim 15, wherein the first rare earth-based cluster comprises a ytterbium-based hexanuclear cluster and the at least one other chemically distinct rare earth-based cluster comprises a neodymium-based hexanuclear cluster and the carboxylic-acid based linker comprises a di-, tri-, tetra-, or hexacarboxylic acid.

17. The optical tag of claim 15, wherein at least one of the first rare earth-based cluster or the at least one other chemically distinct rare earth-based cluster is photoluminescent.

18. The optical tag of claim 15, wherein the mixed cluster heterometallic metal-organic framework is functionalized with one or more phospho-terminated biological molecules.

19. The optical tag of claim 18, wherein the one or more phospho-terminated biological molecules comprises a nucleic acid, protein, or peptide.

20. The optical tag of claim 18, wherein at least one of the one or more phospho-terminated biological molecules is labeled with a fluorophore.

21. The optical tag of claim 18, wherein the one or more phospho-terminated biological molecules comprises a nucleic acid that is labeled with a dye.

22. The optical tag of claim 21, wherein the dye comprises SYBR Gold dye.

* * * * *